United States Patent

Miyagi

[11] Patent Number: 6,048,340
[45] Date of Patent: *Apr. 11, 2000

[54] HIGH-FREQUENCY TREATMENT DEVICE FOR ENDOSCOPE

[75] Inventor: Kunihiko Miyagi, Tokyo, Japan

[73] Assignee: Machida Endoscope Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/684,706

[22] Filed: Jul. 19, 1996

[30] Foreign Application Priority Data

Aug. 3, 1995 [JP] Japan .................................. 7-218095

[51] Int. Cl.$^7$ .................................................. A61B 17/36
[52] U.S. Cl. .............................................. 606/46; 606/41
[58] Field of Search ........................... 606/32–34, 38–52

[56] References Cited

U.S. PATENT DOCUMENTS

| | | | |
|---|---|---|---|
| 4,034,706 | 7/1977 | Cosens et al. | 606/50 |
| 4,936,301 | 6/1990 | Rexroth et al. | 606/45 |
| 5,312,401 | 5/1994 | Newton et al. | 606/42 |
| 5,441,499 | 8/1995 | Fritzsch | 606/46 |

*Primary Examiner*—David M. Shay
*Attorney, Agent, or Firm*—Fish & Richardson P.C.

[57] ABSTRACT

A high-frequency treatment device for an endoscope has an elongated piercing portion. A sleeve-like first electrode is disposed at a distal end portion of this piercing portion. A bar-like second electrode is coaxially disposed within the first electrode. A sleeve-like insulative layer is interposed between the first electrode and the second electrode.

6 Claims, 4 Drawing Sheets

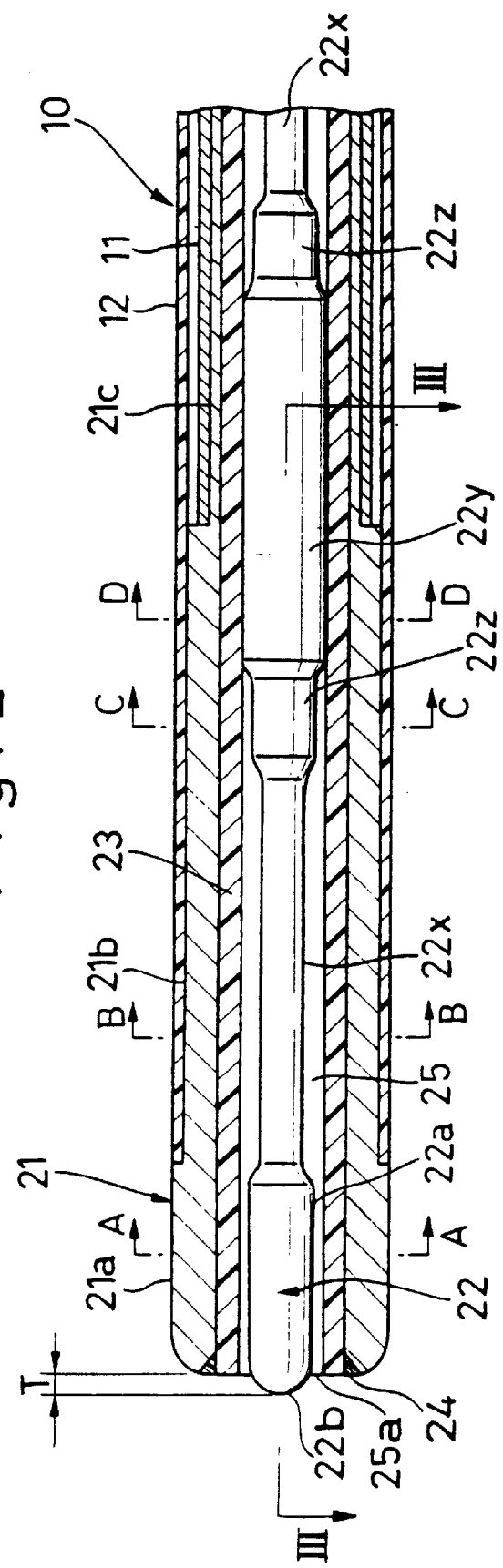

HIGH-FREQUENCY TREATMENT DEVICE FOR ENDOSCOPE

BACKGROUND OF THE INVENTION

This invention relates to a high-frequency treatment device to be pierced into a guide channel of an endoscope.

FIG. 2 of Japanese Patent Application Laid-Open No. 59526/1982 discloses a mono-polar type high-frequency treatment device. FIG. 3 of this publication discloses a bipolar type high-frequency treatment device. In this mono-polar type high-frequency treatment device, a single electrode is disposed within a distal end of an elongated tubular piercing portion. In the bipolar type high-frequency treatment device, a pair of rod-like electrodes are arranged within the distal end of the piercing portion in a spaced and parallel relation.

In the high-frequency treatment device thus constructed, the piercing portion is pierced into the guide channel of the endoscope and a high-frequency current is supplied to the tissue of an organic body through one or two electrodes, with the distal end of the piercing portion projecting from a distal end of the endoscope, to thereby make a treatment to the tissue of the organic body (chiefly, coagulation of the tissue).

Incidentally, in the field of brain surgery or the like, a bipolar type high-frequency treatment device is used because it can supply a high-frequency current to a limited area of the nerve tissue to diminish any adverse effect to the nerve tissue. In this field, there are strong demands for an endoscope to have a more reduced diameter. As this demand is increased, the treatment device to be pierced into the guide channel of the endoscope is increasingly required to have a smaller diameter. However, in the high-frequency treatment device having a pair of parallel bar-like electrodes as mentioned above, it is difficult to reduce the diameter. Moreover, such an arrangement of the electrodes results in a complicated construction.

SUMMARY OF THE INVENTION

It is, therefore, an object of the present invention to provides a high-frequency treatment device for an endoscope which can be reduced in diameter and made simple in construction.

According to the present invention, there is essentially provided a A high-frequency treatment device for an endoscope comprising:

(a) an elongated piercing portion which can be pierced into a guide channel of the endoscope;

(b) a first electrode disposed at a distal end portion of said piercing portion, said first electrode having a sleeve-like configuration; and (c) a second electrode disposed at the distal end portion of said piercing portion, said second electrode having a bar-like configuration and being disposed at a location on an inner side of and radially spaced away from said first electrode.

BRIEF DESCRIPTION OF THE DRAWINGS

FIG. 2 is an enlarged vertical sectional view of that part of FIG. 1 indicated by II;

DETAILED DESCRIPTION OF THE INVENTION

Figure 1:
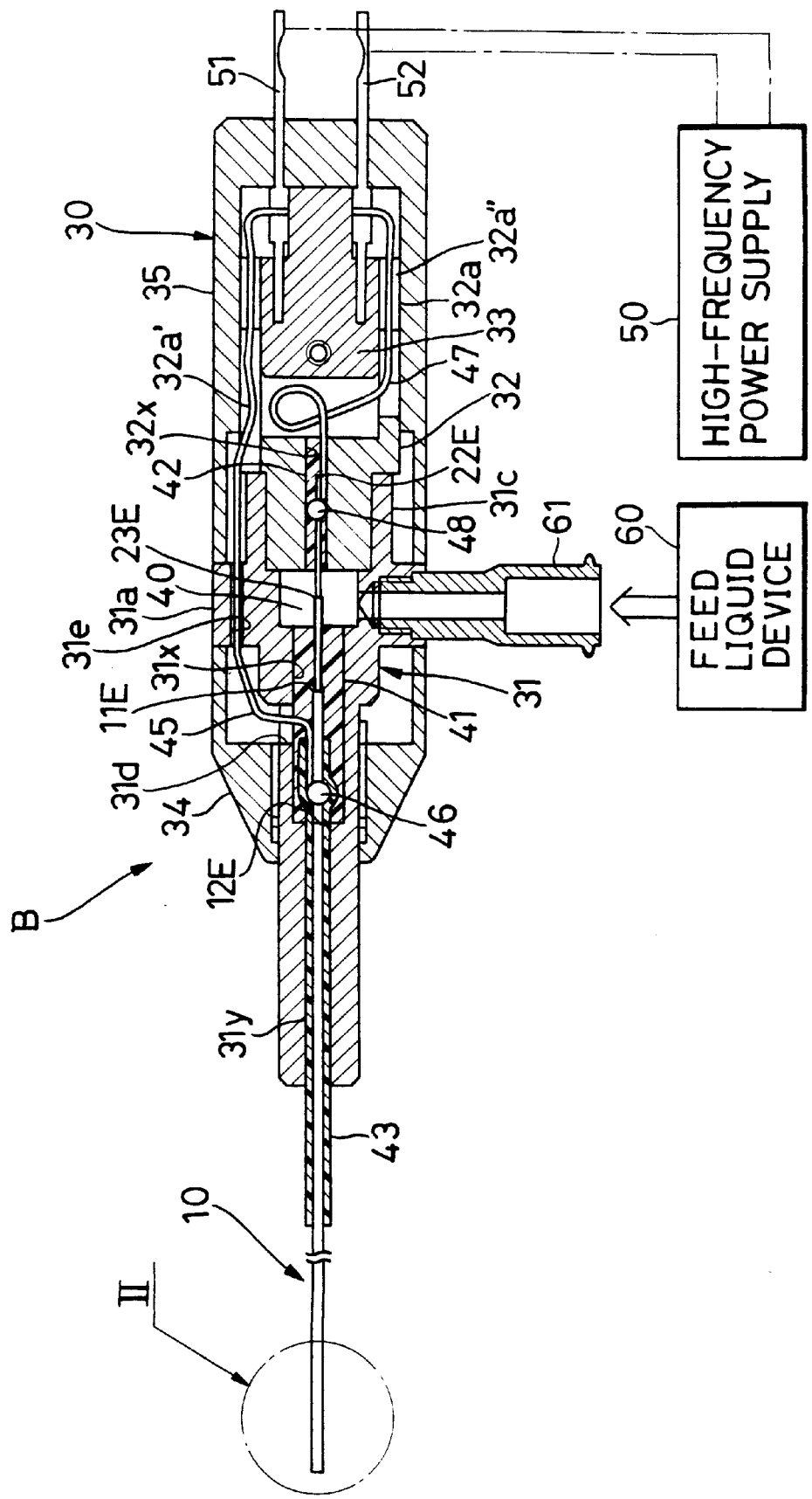
FIG. 1 is a sectional view showing an overall construction of a high-frequency treatment device for an endoscope according to the present invention.
Figure 3D:
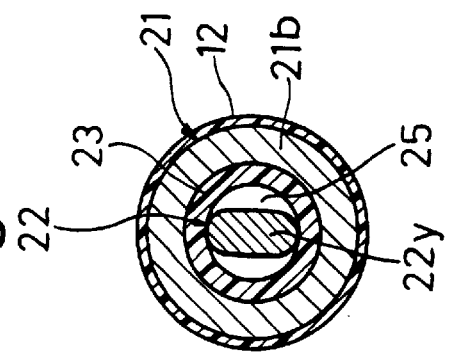
FIGS. 3A–3D is a sectional view taken on line III—III of FIG. 2.
Figure 3C:
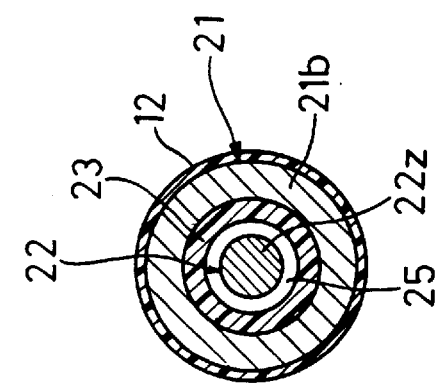
Figure 3B:
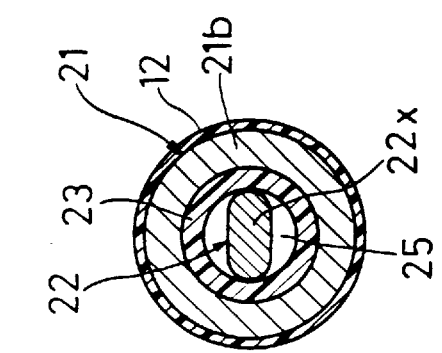
Figure 3A:
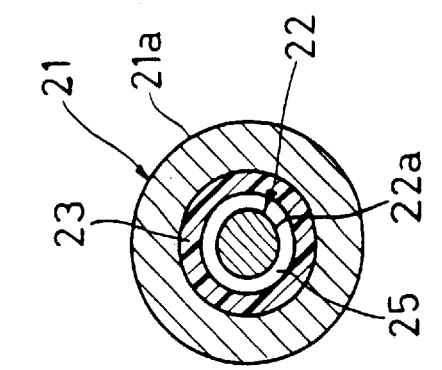
Figure 4:
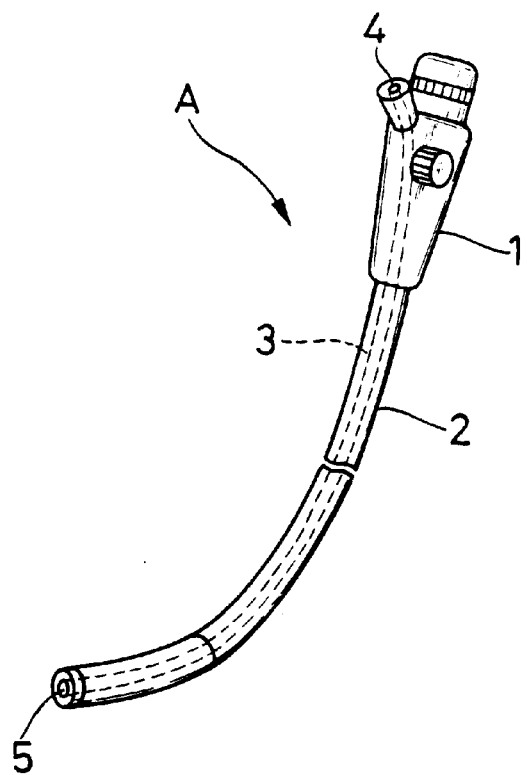
FIG. 4 is a perspective view of an endoscope for which the high-frequency treatment device is used.

A high-frequency treatment device for an endoscope according to one embodiment of the present invention will now be described with reference to FIGS. 1 through 4. First, a known endoscope A of FIG. 4 will be briefly described. The endoscope A comprises a control body 1, and a flexible insertion portion 2 extending from the control body 1. A resin tube is disposed within the control body 1 and insertion portion 2 and constitutes a main part of a guide channel 3. An inlet port 4 of this guide channel 3 is formed in the control body 1, and an outlet port 5 is formed in a distal end face of the insertion portion 2.

A high-frequency treatment device B will now be described. As shown in FIG. 1, the high-frequency treatment device B comprises an elongated flexible tubular piercing portion 10, and a holder 30 disposed on a rear end thereof.

As shown in FIGS. 2 and 3A–3D, a main part of the piercing portion 10 comprises a conductive long flexible tube 11 obtained by spirally winding a strip plate-like metal wire, and an outer jacket tube 12 made of resin covering an outer periphery of the flexible tube 11. A distal end portion of the piercing portion 10 is constituted of a sleeve-like end chip 21 made of metal (having conductive properties). The inner diameter of this end chip 21 is equal over the entire length thereof. The outer diameter of the end chip 21 is steppingly reduced backwardly. The distal end portion 21a having the largest outer diameter is provided as the first electrode. An outer peripheral surface of the first electrode is exposed. A distal end of the outer jacket tube 12 is attached to an outer periphery of an intermediate portion 21b of the end chip 21. A distal end of the flexible tube 11 is mounted on an outer periphery of a rear end portion 21c of the end chip 21 having the smallest outer diameter. The flexible tube 11 and the end chip 21 are electrically connected. The outer diameter of the distal end portion 21a of the end chip 21 is the same as the outer diameter of the outer jacket tube 12. The outer peripheral surface of the end chip 21 is generally continuous with an outer peripheral surface of the outer jacket tube 12.

An insulative tube 23 made of resin is disposed within the piercing portion 10 and extends over the entire length of the piercing portion 10. An adhesive agent 24 is filled in an annular groove formed between an outer periphery of a distal end of this insulative tube 23 and a chamfering of an inner periphery of the distal end of the distal end tube 21. This adhesive agent 24 adheres the insulative tube 23 to the end chip 21, and also serves as a seal therebetween.

A bar 22 made of metal (having conductive properties) is inserted in the insulative tube 23. This bar 22 also extends over the entire length of the piercing portion 10. The bar 22 basically has a circular configuration in section. The inner diameter of the insulative tube 23 is larger than the outer diameter of the bar 22. In other words, a sectional area of an internal space of the insulative tube 23 is larger than a sectional area of the bar 22. For this reason, a gap serving as a feed liquid passage 25 is formed between an inner periphery of the insulative tube 23 and an outer periphery of the bar 22. This feed liquid passage 25 has an opening 25a which is formed between the distal ends of the insulative tube 23 and the bar 22.

A distal end portion 22a of the bar 22 has a circular configuration in section. A distal end face 22b of the bar 22 has a generally semi-spherical surface (convex surface). This distal end portion 22a is provided as a second electrode. The distal end of the bar 22 is projected a predetermined dimension T from the distal end of the end chip 21.

The distal end portion 21a (first electrode) of the end chip 21 and the distal end portion 22a (second electrode) of the bar 22 are away from each other. The distal end portion of the resin tube 23 is provided as an insulative layer for electrically isolating the distal end portion 21a from the distal end portion 22a.

The bar 22 has a plurality first support portions 22x and second support portions 22y alternately arranged backwardly from the distal end portion 22a. Those support portions 22x and 22y are pressed to have a flat configuration in section, and are perpendicular to each other when viewed axially of the bar 22. Those support portions 22x and 22y are away from each other, and a portion 22z located therebetween is not pressed. The portion 22z has a circular configuration in section.

Width-wise opposite side edges of the support portions 22x and 22y are in contact with the inner periphery of the insulative tube 23. This arrangement makes it possible to prevent the distal end portion 22a (second electrode) of the bar 22 from shaking radially. As a consequence, this distal end portion 22a is maintained coaxial with the distal end portion 21a (first electrode) of the end chip 21 to thereby ensure a proper interval therebetween.

In this embodiment, although the plural support portions 22x and 22y are formed in a nearby area of the distal end of the bar 22, they may be one each. Also, they may be alternately formed generally over the entire length of the bar 22.

In this embodiment, the piercing portion 10 is so thin that its outer diameter is about 1 mm. The flexible tube 11 and the outer jacket tube 12, which constitute the piercing portion 10, have of course flexible properties. In addition, the insulative tube 23 made of resin also has flexible properties. The bar 22 is formed of a very thin metal wire having an outer diameter of about 0.3 mm. Accordingly, the piercing portion 10 has sufficient flexibility.

As shown in FIG. 1, the holder 30 includes a first, a second and a third retaining member 31, 32 and 33 which are arranged backwardly in order, and two case members 34 and 35 which are separately located, one at a forward position and the other at a backward position.

An intermediate portion of the first retaining member 31 is threadingly engaged with a distal end portion of the front case member 34, and a distal end portion of the first retaining member 31 projects from the distal end of the front case member 34. A flange portion 31a is formed in the nearby area of a rear end of the first retaining member 31. A rear end of the front case member 34 is in abutment with this flange portion 31a.

A sleeve portion 31c is formed at the rear end of the first retaining member 31, and a distal end portion of the second retaining member 32 is fixedly inserted into this sleeve portion 31c. Another sleeve portion 32a is formed at a rear portion of the second retaining member 32, and the third retaining member 33 is fixedly inserted into this sleeve portion 32a. The rear case member 35 is fixed to an outer periphery of the sleeve portion 32a of the second retaining member 32 by a thread or the like, and a distal end of the rear case member 35 is in abutment with the flange portion 31a of the first retaining member 31. This rear case member 35 covers the second and third retaining members 32 and 33.

Two plugs 51 and 52 are retained by the third retaining member 33. The plugs 51 and 52 extends through a rear end wall of the rear case member 35 and projects backwardly thereof. A high-frequency power supply 50 is connected to the plugs 51 and 52.

A liquid pool chamber 40 is defined by the first and second retaining members 31 and 32. This liquid pool chamber 40 is connected to a feed liquid device 60 through a connecting tube 61 which is threaded into the flange portion 31a of the first retaining member 31.

Holes 31x and 31y are formed in the first retaining member 31 forwardly from the liquid pool chamber 40 in order. The hole 31y has a smaller diameter than the hole 31x. A rear end of the hole 31y is in communication with the hole 31x, and a distal end thereof is opened at a distal end face of the first retaining member 31.

A first resin molded portion 41 is formed by resin which is filled in the hole 31x of the first retaining member 31. A rear end face of the first resin molded portion 41 is faced with the liquid pool chamber 40. An axially extending hole 32x is also formed in a distal portion of the second retaining member 32. A second resin molded portion 42 is formed by resin which is filled in the hole 32x. A distal end face of this second resin molded portion 42 is faced with the liquid pool chamber 40.

A connecting mechanism for connecting the holder 30 with the piercing portion 10 will now be described. The rear end portion of the piercing portion 10 is covered with a short protective tube 43 made of resin and is inserted into the hole 31y of the first retaining member 31 through this protective tube 43. At the rear end portion of the piercing portion 10, a rear end 12E of the outer jacket tube 12, a rear end 11E of the flexible tube 11, a rear end 23E of the insulative tube 23 and the rear end 22E of the bar 22 are arranged backwardly in this order.

The rear end 12E of the outer jacket tube 12 is located at a boundary between through-holes 31x and 31y. The rear end 11E of the flexible tube 11 is at an intermediate location in a longitudinal direction of the through-hole 31x. A nearby area of the rear end of the flexible tube 11 is exposed from the outer jacket tube 12. A distal end of a conductive wire 45 (first conductive wire) is connected to the nearby area of the rear end of the flexible tube 11. This connecting portion 46 is embedded in the first resin molded portion 41. The conductive wire 45 extends from a peripheral surface of the first resin molded portion 41, passes through a hole 31d formed in the peripheral wall of the first retaining member 31, then passes through another hole 31e formed in a flange portion 31a of the first retaining member 31, then passes through a slit 32a' formed in the sleeve portion 32a of the second retaining member 32, and then extends backwardly therefrom. A rear end of the conductive wire 45 is connected to the plug 51.

The insulative tube 23 extends backwardly from the first resin molded portion 41, and the rear end 23E is located at the liquid pool chamber 40. Owing to this arrangement, the opening at the rear end of the feed liquid passage 25 formed between the insulative tube 23 and bar 22 is in communication with the liquid pool chamber 40.

The bar 22 extends further backwardly to enter the through-hole 32x formed in the second retaining member 32, and the rear end 22E is at an intermediate location of the through-hole 32x. Within this through-hole 32x, a distal end of a conductive wire 47 (second conductive wire) is connected to the bar 22, and its connecting portion 48 is embedded in the second resin molded portion 42. The conductive wire 47 passes through the slit 32" formed in the sleeve portion 32a of the second retaining member 32 and extends backwardly therefrom. A rear end of the conductive wire 47 is connected to the plug 52.

As previously mentioned, the liquid pool chamber 40 is closed because the front and rear through-holes 31x and 32y are closed with the molding resin. In other word, the connecting portions 46 and 48 are protected from the liquid in the liquid pool chamber 40 by the molding resin.

As mentioned above, the distant end chip 21 is electrically connected to the plug 51 through the flexible tube 11 and the conductive wire 45. The bar 22 is connected to the plug 52 through the conductive wire 47.

Operation of the high-frequency device B having the above-mentioned construction will now be described. The insertion portion 2 of the endoscope A is inserted into the body cavity of the patient. When the diseased part is found out through the observation of the body cavity using the endoscope A, the piercing portion 10 of the high-frequency treatment device B is pierced through the guide channel 3 of the endoscope A with its distal end allowed to project from the distal end face of the insertion portion 2 of the endoscope A. Owing to this arrangement, the distal end of the end chip 21 of the high-frequency treatment device B (distal end of the first electrode 21a) and the distal end of the bar 22 (distal end of the second electrode 22a) are brought into contact with the tissue of the organic body of the patient. In that state, when a high-frequency current from the high-frequency power supply 50 is supplied through the electrodes 21a and 22a, the area of the tissue of the organic body, which contacts the distal ends of the electrodes 21a and 22a, and its nearby area can be coagulated.

Since the distal end of the second electrode 22a is allowed to project forwardly of the distal end of the first electrode 21a, a favorable contacting state between the two electrodes 21a, 22a and the tissue of the organic body can be maintained. Consequently, the tissue of the organic body can be coagulated in a favorable manner.

When a liquid such as water is fed from the feed liquid device 60 during the course of such a treatment as mentioned above, this liquid enters the liquid pool chamber 40, then passes through the feed liquid passage 25, and is finally fed towards the tissue of the organic body. By this, the coagulated tissue of the organic body can be prevented from sticking to the electrodes 21a and 22a.

As mentioned above, since the liquid from the feed liquid device 60 is fed into the feed liquid passage 25 of the piercing portion 10 via the liquid pool chamber 40, the liquid can be fed in a stable manner regardless how narrow the feed liquid passage 25 is.

In the high-frequency device B having the above-mentioned construction, since the first electrode 21a serving as the distal end of the end chip 21 has a sleeve-like configuration and the second electrode 22a serving as the distal end portion of the bar 22 is arranged in a coaxial relation within the first electrode 21a, the outer diameter of the piercing portion 10 can be reduced compared with the conventional example in which two electrodes are arranged in a parallel relation. Especially, in this embodiment, since the first electrode 21a serves the outermost layer of the distal end portion of the piercing portion 10, the outer diameter of the piercing portion 10 can be made so small as equal to the outer diameter of the first electrode 21a.

The flexible tube 11 has not only the role as a component element of the piercing portion 10 but also as a conductive means for feeding the high-frequency current to the end chip 21. Since no additional conductive means for the end chip is required, the construction can be made simple and the diameter of the piercing portion 10 can be more reduced.

Since the bar 22 extends over the entire length of the piercing portion 10 and its distal end portion serves as the second electrode 22a, no additional conductive means to be connected to the second electrode 22a is required within the piercing portion 10. Accordingly, the construction can be made simple.

Since the insulative tube 23 has not only the role for electrically isolating the bar 22 from the end chip 21 and the flexible tube 11 but also the role for forming the feed liquid passage 25, the number of the component parts can be reduced and the construction can be simplified.

Figure 5:
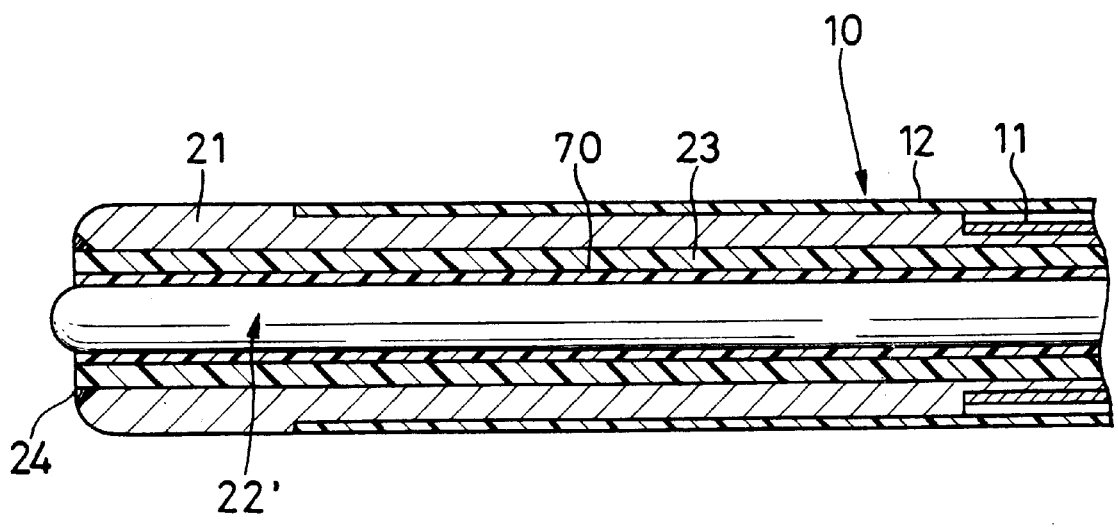
FIG. 5 is a view, like FIG. 2, showing another embodiment of the present invention.

The present invention is not limited to the above embodiments, but many changes can be made. For example, in case no function for feed liquid is required, as shown in FIG. 5, it may be designed such that the bar 22' has a circular configuration in section over the entire length thereof and a resin layer 70 is embedded in the gap between the bar 22' and the insulative tube 23. Since the remaining construction is the same as the above-mentioned embodiments, like component parts are denoted by like reference numerals and description thereof is omitted. The insulative tube 23 and the resin layer 70 may be formed of a single resin tube.

It may be designed such that the first through third support portions of a flat configuration are disposed in order on the bar in the axial direction instead of the support portions 22x and 22y, and those support portions are intersected with each other at 60 degrees when viewed in the axial direction.

The present invention may be applied to a high-frequency treatment device to be used for a hard endoscope. In that case, the piercing portion of the high-frequency treatment device B is not necessarily required to be flexible.

Although the present invention can exhibit its maximum advantages when it is applied to a thin high-frequency treatment device, it may also be applied to a comparatively thick high-frequency treatment device. Even in that case, a simple construction can be enjoyed.

What is claimed is:

1. A high-frequency treatment device for an endoscope comprising:

an elongated piercing member insertable into a guide channel of the endoscope, the piercing member having a proximal end portion, a distal end portion, and a tubular passageway extending therethrough;

a tubular electrode disposed at the distal end portion of the piercing member;

an insulation tube interposed in the tubular passageway; and a conductive bar having a substantially round sectional configuration and being concentrically received inside the insulation tube, the conductive bar comprising:

a bar electrode disposed at the distal end portion of the piercing member, the bar electrode being concentrically received inside the tubular electrode, and first and second support portions each having a substantially flat sectional configuration, the first and second support portions being arranged in order in an axial direction and intersecting when viewed in the axial direction, and the first and second support portions each having edges in contact with an inner peripheral surface of the insulation tube to support the bar electrode in coaxial alignment with the tubular electrode;

wherein the insulation tube includes a first end portion interposed between the tubular and bar electrodes, the first end portion comprising an electrical insulation layer between the tubular and bar electrodes; and a feed fluid passage is formed between the outer surfaces of the conductive bar and the inner peripheral surface of the insulation tube, the feed fluid passage being accessible from the distal end portion of the piercing member.

2. A high-frequency treatment device for an endoscope according to claim 1, wherein a distal end of the bar electrode projects outwardly relative to a distal end of the tubular electrode.

3. A high-frequency treatment device for an endoscope according to claim 1, further including a hollow holder located at the proximal end portion of the piercing member, the hollow holder having a first resin molded portion and a second resin molded portion separated by a liquid pool chamber, the first resin molded portion having a first conductive wire and the second resin molded portion having a second conductive wire; and wherein:

the distal end portion of the piercing member is provided with a conductive sleeve having a distal end portion which acts as the tubular electrode;

the piercing member includes a conductive, elongated flexible tube and an outer jacket resin tube covering an outer periphery of the flexible tube, the flexible tube and the outer jacket resin tube having first ends mounted on the conductive sleeve, the flexible tube having a second end connected to the first conductive wire;

the insulation tube includes a second end portion disposed within the liquid pool chamber to permit fluid communication between the feed liquid passage and the liquid pool chamber; and the conductive bar has a second end portion connected to the second conductive wire.

4. A high-frequency treatment device for an endoscope according to claim 1, wherein the first and second support portions are away from each other in the axial direction.

5. A high-frequency treatment device for an endoscope according to claim 1, wherein the distal end portion of the piercing member is provided with a conductive sleeve having a distal end portion which acts as the tubular electrode, and wherein an outer peripheral surface of the tubular electrode is exposed.

6. A high-frequency treatment device for an endoscope according to claim 5, wherein the piercing member includes a conductive, elongated flexible tube and an outer jacket resin tube covering an outer surface of the flexible tube, the flexible tube and outer jacket resin tube having distal ends mounted on the conductive sleeve, a high-frequency power source being connected between rear ends of the conductive bar and the flexible tube.

* * * * *